United States Patent [19]
Lai et al.

[11] Patent Number: 5,591,576
[45] Date of Patent: Jan. 7, 1997

[54] STEROL Δ14 REDUCTASE SCREEN

[75] Inventors: Margaret H. K. Lai, E. Brunswick; Donald R. Kirsch, Princeton, both of N.J.; Martin Bard, Carmel, Ind.

[73] Assignee: American Cyanamid Company, Wayne, N.J.

[21] Appl. No.: 107,348

[22] Filed: Aug. 16, 1993

[51] Int. Cl.$^6$ .......................... C12N 15/63; C12Q 1/02; C12Q 1/26; C12Q 1/68
[52] U.S. Cl. .................. 435/6; 435/25; 435/29; 435/32; 435/254.21; 435/254.4; 435/320.1
[58] Field of Search .................................. 435/32, 320.1, 435/25, 6, 29

[56] References Cited

PUBLICATIONS

Marcireau et al., Antimicrobial Agents and Chemotherapy, 34:989–993 (1990).
Ashman, W. H., et al., Lipids 26:628–632 (1991).
Baloch, R. and Mercer, I., Phytochemistry 26: 663–668 (1987).
Brugge, J. S., et al., Mol. Cell. Biol. 7:2180–2187 (1987).
Ellis, S. W., et al., J. Gen. Micro. 137:2627–2630 (1991).
Grindle, M., and Farrow, R., Mol. Gen. Genet. 165:305–308 (1978).
Kyte, J., and Doolittle, R. F., J. Mol. Biol. 157: 105–132 (1982).
Lorenz, T., and Parks, L. W., DNA and Cell Biol. 11: 685–692 (1992).
Marcireau, C., et al., Curr. Genet. 22: 267–272 (1992).
Mercer, E. I., Biochem. Soc. Trans. 19: 788–308 (1991).
Nasmyth, K. A., and Tatchell, K., Cell 19: 753–764 (1980).
Paltauf, F., et al., in Jones, E. W., et al., eds., The Molecular and Cellular Biology of the Yeast Saccharomyces, Gene Expression, Cold Spring Harbor Laboratory Press, 1992, pp. 415, 418–420, 424–428 and 434–437.

*Primary Examiner*—Robert A. Wax
*Assistant Examiner*—Eric Grimes
*Attorney, Agent, or Firm*—Darryl L. Webster; Mary Krinsky

[57] ABSTRACT

A binary assay identifies agents that inhibit sterol Δ14 reductase involved in ergosterol biosynthesis. In the primary screen, sterol Δ14 reductase inhibition by a test sample is assayed by adding the test sample to a culture of *Neurospora crassa* having an erg-3 mutation and also to a culture of a strain having an erg-1 mutation, comparing the extent of growth inhibition after incubation in the two cultures, and identifying as positives those samples that show growth inhibition in the erg-3 culture exceeding that in the erg-1 culture. In the secondary screen, samples that test positive in the primary screen are reassayed by adding the test sample to a culture of a *Saccharomyces cerevisiae* strain into which has been introduced multiple copies of a gene encoding sterol Δ14 reductase and also to a strain of *S. cerevisiae* that does not have the introduced gene; positive samples are identified after incubation by observation that growth inhibition in the culture having no introduced reductase gene exceeds growth inhibition in the culture having the introduced reductase gene. In preferred embodiments, a known inhibitor of sterol Δ14 reductase is employed in solidified media in both the primary and the secondary screens, resulting in an assay that is highly sensitive and specific for the detection of sterol Δ14 reductase inhibitors.

21 Claims, 2 Drawing Sheets

STEROL Δ14 REDUCTASE SCREEN

TECHNICAL FIELD OF THE INVENTION

This invention relates to a screening method for the identification of agents that inhibit the sterol Δ14 reductase enzyme of sterol biosynthesis.

BACKGROUND OF THE INVENTION

Sterols are steroid alcohols of vegetable and animal origin. Ergosterol is the principal membrane sterol of fungi. It is structurally similar to its animal counter-part, cholesterol, and its higher plant counter-parts, stigmasterol and sitosterol. Though the biosynthesis of ergosterol in fungi involves steps distinct from the other sterols, the pathways in different organisms share several common steps. The lanosterol 14α-demethylation steps in cholesterol and ergosterol formation in animals and fungi, as well as the obtusifoliol 14α-demethylation in stigmasterol and sitosterol biosynthesis in plants, both lead to the formation of a double bond between carbons 14 and 15 of the sterol ring. This double bond is then reduced by sterol Δ14 reductase activity. The enzyme is located in the microsomal fraction in pig liver, yeast and *Zea mays*, and requires NADPH as an electron donor (Marcireau, C., et al., *Curr. Genet.* 22: 267–272 (1992)).

Genetic studies of ergosterol biosynthesis mainly have been carried out in Saccharomyces cerevisiae (Paltauf, F., et al., in Jones E. W., et al., eds., *The Molecular and Cellular Biology of the Yeast Saccharomyces, Gene Expression*, Cold Spring Harbor Laboratory Press, 1992, pages 434–437). In yeast, ergosterol affects membrane fluidity and permeability and plays an essential role in the yeast cell cycle. Mutations in the biosynthetic pathway are generally recovered by selecting for resistance to polyene antibiotics. Polyenes bind to ergosterol in the plasma membrane and produce pores through which ions can flow leading to cell death. Mutants with lower levels of plasma membrane ergosterol bind less polyene and show increased resistance. This method has permitted the recovery of mutations in many of the genes in the pathway.

A series of polyene-resistant mutants of *Neurospora crassa* were isolated several years ago, although little work was done at that time to characterize the mutations on a molecular level. Recently, Grindle and co-workers characterized one of these *Neurospora crassa* mutants, denoted erg-3, and found that it carried a genetic lesion in sterol Δ14 reductase activity (Ellis, S. W., et al., *J. Gen. Micro.* 137: 267–272 (1992)). The sterol Δ14 reductase gene in *S. cerevisiae*, denoted ERG24, also has recently been cloned and sequenced (Lorenz, T., and Parks, L.W., *DNA and Cell Biol.* 11: 685–692 (1992)).

Toward the end of the biosynthetic pathway of ergosterol biosynthesis, sterol Δ14 reductase and Δ8–Δ7 isomerase catalyze steps in the conversion of lanosterol to ergosterol. After ignosterol is reduced by sterol Δ14 reductase, the sterol is demethylated and rearranged to fecosterol, which is then isomerized by sterol Δ8–Δ7 isomerase. Mechanism of action studies indicate that several morpholine and structurally related piperidine compounds having large ring N-substituents such as dodemorph, tridemorph, aldimorph, fenpropimorph, amorolfine, and fenpropidin, currently marketed as fungicides, act via the inhibition of these two enzymes (Mercer, E.I., *Bio chem. Soc. Trans.* 19: 788–308 (1991)). This conclusion stems in part from the observation that substrates for the enzymes build up in fungal cells treated with low levels of the fungicides. However, it recently has been found that the sterol Δ8–7 isomerase gene is not essential for viability in *S. cerevisiae* (Ashman, W. H., et al., *Lipids* 26: 628–632 (1991)), suggesting that the killing effect of morpholine fungicides may be primarily the result of sterol Δ14 inhibition.

SUMMARY OF THE INVENTION

It is an object of the invention to provide a screening test for the identification of agents exhibiting sterol biosynthesis inhibition.

It is another object of the invention to provide a screening test to identify agents exhibiting potential fungicidal activity for a wide variety of agricultural, medical, and veterinary uses.

It is a further and more specific object of this invention to identify agents that inhibit the sterol Δ14 reductase reaction in the ergosterol biosynthetic pathway.

These and other objects are accomplished by the present invention, which provides a method for the identification of agents which inhibit sterol Δ14 reductase involved in ergosterol biosynthesis. The method is a screening test that, in the most preferred embodiment, involves a primary and a secondary screen. In the primary screen, sterol Δ14 reductase inhibition by a test sample is assayed by adding the test sample both to a culture of a *Neurospora crassa* strain having an erg-3 mutation (such as FGSC2725) and to a culture of a *Neurospora crassa* strain having an erg-1 mutation (such as FGSC2721). The samples are incubated for such time under such conditions sufficient to observe fungal cell growth in corresponding cultures containing no test sample, and the extent of growth inhibition in the two cultures is compared. Sterol Δ14 reductase inhibition is determined by observing that growth inhibition in the erg-3 culture containing the test sample exceeds growth inhibition in the erg-1 culture containing the test sample. In preferred embodiments, a known inhibitor of sterol biosynthesis such as tridemorph or fenpropimorph is added to solidified cultures as a control, and test and control samples are added on a disk or in a well so that inhibition can be easily observed visually.

In the secondary screen, samples that test positive in the primary screen are reassayed by adding the test sample to a culture of a *Saccharomyces cerevisiae* strain into which has been introduced multiple copies of a gene encoding sterol Δ14 reductase such as strain Y294(pML100), and also to a culture of a corresponding *Saccharomyces cerevisiae* strain which does not have an introduced sterol Δ14 reductase gene such as Y294(YEp13). The samples are incubated in the cultures for such time under such conditions sufficient to observe yeast cell growth in corresponding cultures containing no test sample, and the extent of growth inhibition is compared. The presence of sterol Δ14 inhibition is determined by observation that growth inhibition in the culture having no introduced reductase gene exceeds growth inhibition in the corresponding culture having the introduced reductase gene. In preferred embodiments, a known inhibitor of sterol Δ14 reductase, such as fenpropimorph, is added to solidified cultures as a control, and test and control samples are added on a disk or in a well so that inhibition can be easily observed visually.

Each screen can be employed independently to assay for sterol Δ14 reductase inhibition. However, the *N. crassa* screen is less specific than the *S. cerevisiae* screen, and the *S. cerevisiae* screen is less sensitive than the *N. crassa* screen. Therefore, preferred embodiments employ both screens. When carried out together, the binary assay comprising the two screens is highly sensitive and specific for the detection of sterol Δ14 reductase inhibitors.

DETAILED DESCRIPTION OF THE INVENTION

Figure 1:
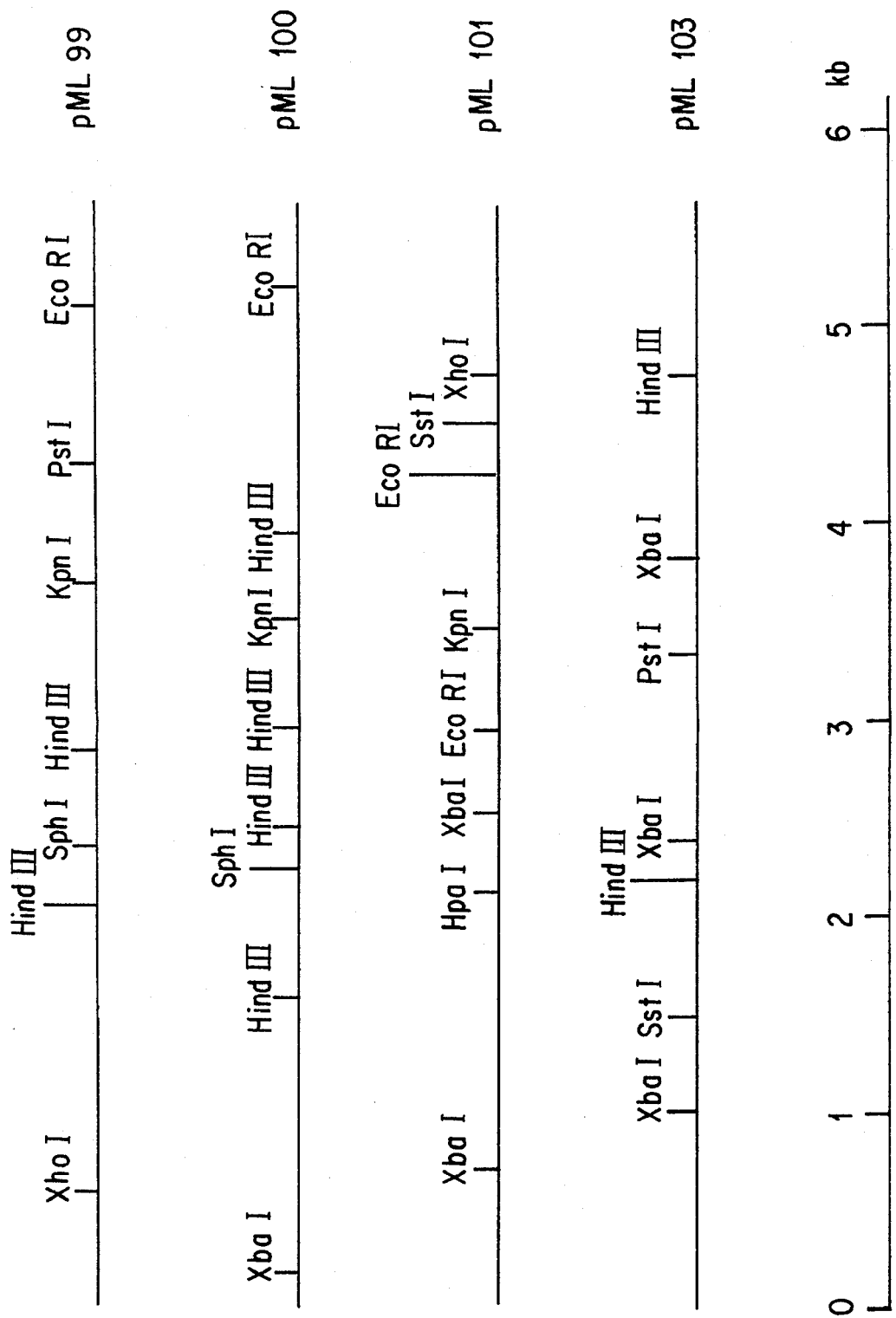
FIG. 1 shows restriction maps of four plasmid inserts recovered via selection for fenpropimorph resistance in *Saccharomyces cerevisiae* as described in Example 2. Selected restriction enzyme digestion sites are shown for each insert.

This invention is based upon the finding that a pair of *Neurospora crassa* mutants defective in ergosterol biosynthesis enzymes are useful in a sensitive and reasonably specific assay for sterol Δ14 reductase inhibition. A second, less sensitive screen employing a *Saccharomyces cerevisiae* strain into which has been introduced a gene encoding sterol Δ14 reductase at high copy is also useful and reasonably specific for sterol Δ14 reductase inhibitors. When carried out together, the screens are highly sensitive and specific for the detection of sterol Δ14 reductase inhibitors.

Two *Neurospora crassa* mutants defective in ergosterol biosynthesis are employed in screening according to the method of the invention. One is an erg-1 mutant defective in sterol Δ8–Δ7 isomerase and the other is an erg-3 mutant defective in sterol Δ14 reductase. Any *N. crassa* erg-1 or erg-3 mutants may be used, such as, for example, those prepared by Grindle, et al., by ultraviolet mutagenesis of wild-type Neurospora (Ellis, E. W., et al., cited above, and Grindle, M., and Farrow, R., *Mol. Gen. Genet.* 165: 305–308 (1978)). Strains may also be obtained from the Fungal Genetics Stock Center (FGSC). In one embodiment, erg-1 mutant FGSC2721 and erg-3 mutant FGSC2725 are employed.

Erg-3 mutants are much more sensitive to morpholinetype fungicides (morpholines and structurally related piperidines) than the wild-type parent strain. For example, in morpholine sensitivity comparisons in cultured plates, the following differences in the size of zone inhibition are obtained in the lawns of the cultures:

| Strain | Description | Size of Inhibition Zone | | |
|---|---|---|---|---|
| | | Tridemorph | Fenpropimorph | Fenpropidin |
| 2490 | wild-type | 27.5 mm | 28.0 mm | 24.5 mm |
| 2721 | erg-1 | 28.5 mm | 30.5 mm | 33.0 mm |
| 2725 | erg-3 | 38.5 mm | 38.0 mm | 37.0 mm |

However, the erg-3 mutant strain also shows increased sensitivity to a large number of compounds with varied mechanisms of action, perhaps due to general increased plasma membrane permeability exhibited by the strain. To control for this effect, the erg-1 mutant strain, which, as illustrated in the above data, shows a fairly normal level of sensitivity to morpholine-type fungicides relative to the wildtype and is more sensitive to other compounds, is used as a control in the screen.

In the practice of the screening method for the presence or absence of sterol biosynthesis inhibition by a test sample using the method of the invention, the test sample is added to a culture of a *Neurospora crassa* strain having an erg-3 mutation and also to a second culture of a *Neurospora crassa* strain having an erg-1 mutation. The samples are incubated in the cultures for such time under such conditions sufficient to observe fungal cell growth in corresponding cultures containing no test sample. In preferred embodiments, sterol Δ14 reductase inhibitors are added to both cultures as controls. The extent of growth inhibition in the culture containing the erg-3 mutation is then compared with the extent of growth inhibition in the culture containing the erg-1 mutant. The presence of sterol biosynthesis inhibition, particularly sterol Δ14 reductase inhibition, is determined by observation that growth inhibition in the erg-3 culture exceeds growth inhibition in the erg-1 culture.

Any type of solidified or liquid media that will support growth and reproduction of the *N. crassa* strains may be employed as cultures in the method of this invention. Numerous media are known to the skilled artisan, and an advantage of the invention is that the ascomycete fungus has been studied rather extensively and grown in a variety of conditions. Conidia suspensions can be stored for weeks. Example media include Difco Neurospora Minimal Media, Vogel's Media containing salts, sucrose and biotin, and yeast media containing yeast extract and sorbose. Example media are provided hereinafter.

Where liquid cultures are employed, differences in growth are generally determined by observing and comparing turbidity; for this purpose, optical density (OD) readings at 550 to 650 nm are made and compared. Preferred media, however, are solidified by adding agar or gelatin forming cultures in plates or dishes. Agar is especially preferred.

In preferred embodiments, a positive control is employed to assist in the identification of potential agents. In these embodiments, a known inhibitor of sterol biosynthesis is employed. For example, a known sterol Δ14 reductase inhibitor such as tridemorph, fenpropimorph, or fenpropidin is useful as a control. Positive controls are added to cultures or culture areas of both *N. crassa* strains, and the control effects on culture growth are compared to the cultures or culture areas with the test samples. Tridemorph is preferred in one embodiment; in solidified cultures, a 200 ng tridemorph disk gives a clear differential response.

As mentioned above, particularly preferred embodiments employ solidified media, so that test samples and positive controls are observed visually and simultaneously as regions of the same culture. Samples or controls are introduced on a disk or in a well of the plate. Inhibition is observed visually as measurable zones around disks or wells in the lawn of growth in the plate or dish. Actives produce a larger zone around test samples grown in a lawn of the erg-3 strain than in a lawn of the erg-1 strain.

A distinct advantage of this screening method is its speed and simplicity. The protocol is simple. Many samples are readily analyzed in a short time, providing new potential sterol biosynthesis inhibitors, notably sterol Δ14 reductase inhibitors. The inhibitors can be employed in the arsenal against undesirable fungi, some of which are resistant to currently known fungicides, and interfere with pathogen but not host metabolism.

It is another advantage of this screening method that it is sensitive, and only small amounts of biochemical or chemical agents are required for the test. In a standard assay, for example, which employs solidified media in a plate, as little as 10 ng fenpropimorph or fenpropidin, and 20 ng of tridemorph are detected.

As revealed in screens of over 7000 compounds set out in Example 1 below, the assay is not completely selective, however, and a few compounds that are not inhibitors of ergosterol biosynthesis test positive. Therefore, preferred embodiments employ the assay only as a primary screen. Compounds testing positive in the screen are then reassayed with a *Saccharomyces cerevisiae* ergosterol Δ14 reductase assay as a secondary screen.

In the *Saccharomyces cerevisiae* screening method for the presence or absence of sterol Δ14 reductase inhibition by a test sample, the test sample is added to a culture of a *S. cerevisiae* strain into which has been introduced a gene encoding sterol Δ14 reductase, preferably at high copy. The test sample is also added to a culture of a corresponding *S. cerevisiae* strain which does not have an introduced sterol Δ14 reductase gene. The samples are incubated in the cultures for such time under such conditions sufficient to observe yeast cell growth in corresponding cultures containing no test sample, and the extent of growth inhibition in the culture having the reductase gene is compared with the extent of growth inhibition in the culture having no introduced gene. The presence of sterol Δ14 reductase inhibition is determined by observation that growth inhibition in the culture having no introduced reductase gene exceeds growth inhibition in the culture having the introduced reductase gene.

Any *S. cerevisiae* strain into which has been introduced a gene encoding sterol Δ14 reductase can be employed in the screen. Typical strains are obtained by cloning the sterol Δ14 reductase gene and integrating it at multiple sites into the chromosome of wild-type or parental strains, or by transforming a wild-type or parental strain with a multi-copy plasmid encoding the enzyme. The gene has been cloned by selecting strains resistant to fenpropimorph and fenpropidin as set out in Example 2 below and in Lorenz, T., and Parks, L. W., *DNA and Cell Biol.* 11: 685–692 (1992) and in Marcireau, et al., cited above. Sterol analysis of mutants carrying the disrupted gene demonstrate the accumulation of the sterol Δ14 reductase substrate, ignosterol. Cloned genes have been sequenced (ID SEQ NO. 1 set out hereinafter) and found to be substantially identical (Lorenz and Parks, cited above, and Example 2 below), encoding a 438 amino acid, 50.5 kilodalton, basic (pI=9.2) protein. Preferred strains are morpholine resistant when the gene is introduced at high copy.

In the practice of the invention, growth inhibition by a test sample in the yeast strain having an introduced sterol Δ14 reductase gene, such as strain Y294 transformed with a plasmid encoding the gene, such as pML99, pML00, pML101 or pML103, particularly pML100, (described in detail hereinafter), is compared to another strain such as a corresponding wild-type or parental strain having no introduced gene. A parental strain exhibiting similar growth characteristics but having no introduced gene is preferred for the comparison. Where strain Y294(pML100) is employed as the strain having the reductase gene, for example, another Y294 strain is used in the screen, most preferably a strain transformed with a similar plasmid that does not encode the gene. An example illustrated below employs Y294(YEp13) in screens with Y294(pML100).

Any type of solidified or liquid media that will support growth and reproduction of the *S. cerevisiae* strains may be employed as cultures in the method. Numerous yeast media are known to the skilled artisan, and an advantage of the invention is that baker's yeast is relatively easy to grow. Typical media are yeast extract, peptone and dextrose (YEPD) or yeast extract and dextrose (YED) media; yeast basal growth media (YBGM) containing glucose, vitamins, minerals, and water; yeast extract, peptone, and adenine sulfate (YPA) media; yeast mannitol (YM) media and YM plus glucose; synthetic dextrose (SD) media containing dextrose, a nitrogen base, water, and, optionally amino acids, adenine sulfate and uracil; and the like. Example media are provided hereinafter.

Where liquid cultures are employed, differences in growth are generally determined by observing and comparing turbidity; for this purpose, optical density (OD) readings at 550 to 650 nm are made and compared. Preferred media, however, are solidified by adding agar or gelatin to form cultures in plates or dishes. Agar is especially preferred. In these embodiments, differential growth between the strains is observed visually and simultaneously as regions of the same culture. Samples are introduced on a disk or in a well of the plate. Inhibition around the disk or well in the lawn of growth of the strain having the gene is compared to inhibition around the disk or well in the lawn of the strain that does not have the introduced gene. Actives produce a smaller zone on the strain with the gene than in the other strain.

In preferred embodiments, a positive control is employed to assist in the identification of potential agents. In these embodiments, a known inhibitor of sterol Δ14 reductase is employed, such as, for example, fenpropimorph, fenpropidin, tridimorph, or azasterol or a mixture of these. Fenpropimorph is preferred in one embodiment. Positive controls are added to cultures or culture areas of both *S. cerevisiae* strains, and the effects of the control on culture growth are compared to the cultures or culture areas with the test samples to assess activity of test samples on the two strains.

As previously noted, the secondary screen can, in some embodiments, be employed as a primary screen for sterol Δ14 reductase inhibitors. However, since *S. cerevisiae* is naturally less sensitive to morpholines than *N. crassa*, the assay is intrinsically less sensitive than the primary screen using *N. crassa* described above. Therefore, as set out above, the *S. cerevisiae* screen is preferably employed as a secondary screen to test positive samples from the *N. crassa* primary screen.

Morpholines are detected in the *S. cerevisiae* screen at about 12.5 μg/disk for fenpropimorph and fenpropidin and 50 μg/disk for tridimorph. As a result, in preferred embodiments, actives from the *N. crassa* primary screen are concentrated about 2500-fold prior to testing in the secondary screen. As set out in Example 3 hereinafter, all of the actives from the primary screen with undesired mechanisms of action are inactive in the secondary assay. Hence, when carried out together, the two screens are highly sensitive and specific for the detection of sterol Δ14 reductase inhibitors.

The binary sterol Δ14 reductase assay exhibits a low positive rate assay if compounds which do not inhibit sterol Δ14 reductase in the primary screen are eliminated using the secondary screen. Other tests are, therefore, not of high importance. However, standard in vitro and in vivo fungicide discovery screens are employed in some embodiments as tertiary tests to prioritize actives from the binary assay.

The in vitro screens test samples for their ability to inhibit the growth of selected phytopathogenic fungi cultured in nutrient agar. Three of these species typically employed, *Pseudocercosporella herpotrichoides* causing wheat eyespot, *Rhizoctonia solani* causing rice sheath blight, and *Fusarium oxysporum* causing damping off, synthesize ergosterol. In practice, fenpropomorph and tridemorph are primarily active in vitro against *Rhizoctonia solani* in the 1 ppm range (1 μg/ml), while fenpropimorph is detected at ~10 ng/ml in the sterol Δ14 reductase primary screen if 30

μl volumes are tested in welled plates. Thus, fermentations in the in vitro screen are generally retested after about a 200-fold concentration.

In in vivo screens, a variety of phytopathogenic fungi are used to infect plants treated with test compounds. Active compounds block or reduce the appearance of disease symptoms. A number of model plant infections are employed in the screen and include fungi that cause apple scab (*Venturia inaequalis*), grape downy mildew (*Botrytis cinerea*), pepper botrytis (*Botrytis cinerea*), rice blast (*Pyricularia oryzae*), sugar beet cercospora (*Cercospora beticola*), tomato early blight (*Alternaria solani*), wheat leaf rust (*Puccinia recondita tritici*), and wheat powdery mildew (*Erysiphe graminis tritici*). The most potent test compounds in these assays are active in the 10 ppm range. When morpholines are specifically tested in this screen, fenpropimorph and tridemorph are active at about 10 ppm, mainly against the powdery mildews. These data indicate that extensive concentration (~2000 fold) are necessary to evaluate actives from this tertiary screen. All of the species in this test except one, *Plasmopara viticola*, grape downy mildew, synthesize ergosterol and are potential targets for ergosterol synthesis inhibitors.

The following examples are presented to further illustrate and explain the present invention and should not be taken as limiting in any regard. As used herein, fungal strains obtained from the Fungal Genetics Stock Center, University of Kansas Medical Center, Kansas 66103, USA are denoted "FGSC". Strains from the American Type Culture Collection, 12301 Parklawn Drive, Rockville, Md. 20852, USA, are denoted "ATCC". Fenpropimorph, fenpropidin and tridemorph are purchased from Crescent Chemical Company, Inc., Hauppauge, N.Y. Synthetic dextrose (SD) media contains 0.7% yeast nitrogen base without amino acids, 2% dextrose and 2% agar. Yeast extract, peptone and dextrose (YEPD) media contains 1% yeast extract, 2% peptone, 2% dextrose and 2% agar.

These examples employ both *Saccharomyces cerevisiae* and *Neurospora crassa*. To avoid confusion between the nomenclature of these two species, the gene correspondence of ergosterol biosynthetic pathway enzymes is as follows:

| Enzyme | *S. cerevisiae* Gene | *N. crassa* Gene |
| --- | --- | --- |
| Δ14 reductase | ERG24 | erg-3 |
| C-24 methyl transferase | ERG6 | erg-4 |
| Δ8-Δ7 isomerase | ERG2 | erg-1 |
| C-24(28) reductase | ERG4 | erg-2 |

(see Paltauf, et al., Grindle and Farrow, and Lorenz and Parks references cited above).

EXAMPLE 1

This example describes a sterol Δ14 reductase primary screen using erg-1 and erg-3 *Neurospora crassa* strains.

Fungal strains FGSC2721 (erg-1) and FGSC2725 (erg-3) are cultured as follows. A suspension of conidia stored at 4° C. in 0.005% Tween® 80 is stable for at least 6 weeks. Every 6 to 8 weeks, a fresh culture is prepared by coating the lower half of three 250 ml Erlenmeyer flasks with Neurospora minimal media or Vogel's minimal media described below. This is most easily accomplished by adding 25 ml molten agar media with 12.5 units of nystatin for FGSC2725 and 25 ml molten agar media for FGSC2721 to each flask, then tilting the flask in an ice bath, and rolling it quickly until the agar hardens in an even coating. A few drops (~0.1–0.2 ml) of culture or conidial suspension are added to each flask, and spread around to evenly wet the agar surface by rolling the flask. The flasks are incubated for 2 to 3 days in the dark (e.g., foil wrapped) at room temperature or 37° C. When generous aerial growth is obtained, the unwrapped flasks are placed under a fluorescent lamp or placed by a window to induce sporulation. The orange conidia can be harvested after 5 or more days by rinsing the flasks twice with 5 ml 0.005% Tween® 80 and a small quantity of 0.3 mm glass beads. Yields should be ~30 ml, at $0.5-1.0 \times 10^8$ spores per ml (determined using a hemocytometer). Working stock solution for the screen should be adjusted to ~$1 \times 10^7$ spores per ml 0.005% Tween® 80.

Neurospora minimal media is prepared by combining

| Difco Neurospora Minimal Media | 27.7 gm |
| --- | --- |
| Difco Agar | 20.0 gm |
| Distilled Water | 1000 ml | and autoclaving 15 minutes at 20 pounds pressure.

Vogel's minimal media is prepared as set out below. A trace minerals solution is first prepared for use as an ingredient in the stock salts solution, by adding in order, to 95 ml distilled water with continuous stirring:

| Citric Acid.$H_2O$ | 5 g |
| --- | --- |
| $ZnSO_4.7H_2O$ | 5 g |
| $Fe(NH_4)_2(SO_4)_2.6H_2O$ | 1 g |
| $CuSO_4.5H_2O$ | 0.25 g |
| $MnSO_4.H_2O$ | 0.05 g |
| $H_3BO_3$ | 0.05 g |
| $NaMoO_4.2H_2O$ | 0.05 g |

The solution is stored at room temperature over 1 ml chloroform.

A liter of a 50X Stock Salts Solution is prepared by dissolving the following, in order, with continuous stirring, in 750 ml distilled water:

| Sodium Citrate.5½$H_2O$ | 150 g |
| --- | --- |
| $KH_2PO_4$ | 250 g |
| $NH_4NO_3$ | 100 g |
| $MgSO_4.7H_2O$ | 10 g |
| $CaCl_2.2H_2O$ | 5 g |
| Trace Minerals Solution | 5 ml |
| Biotin (0.1 mg/ml) | 2.5 ml |

The pH of the solution is adjusted to ~5.8 and distilled water is added to a final volume of 1 liter. The solution is stored at room temperature over 2 ml chloroform.

To prepare Vogel's media, combine

| | Vogel's 5OX Salts Solution | 20 ml |
| --- | --- | --- |
| | Sucrose | 15 gm |
| | Agar | 20 gm |
| and add | Distilled Water to | 1000 ml. |

Autoclave 15 minutes at 20 pounds.

Media for the primary sterol Δ14 reductase screen is prepared by combining

| Yeast Morphology Agar | 35 gm |
| --- | --- |
| Yeast Extract | 1 gm |

| | | |
|---|---|---|
| and adding | L-Sorbose | 25 gm |
| | Distilled Water to | 1000 ml. |

The innocula are the counted suspensions of FGSC2725 and FGSC2721 spores. Working stocks are $5\times10^6$ to $1\times10^7$ spores/ml as described above. One part spores is added to 100 parts media.

For the screen, plates are poured and dried before duplicate test samples are each added to a FGSC2725 plate and a FGSC2721 plate. Each test should include a positive control that gives a clear response such as a 200 ng tridemorph disk. The plates are incubated 48 hours at 37° C. Positives are scored by comparing growth inhibition zones on test and control plates; zones should be larger on the plate inoculated with strain FGSC2725 than on the plate inoculated with strain FGSC2721.

Two panels of compounds, one containing the fungicides and other pesticides having different mechanisms of action as set out in Table 1, and a Second containing 117 antibiotics and antifungals listed in Table 2, are tested using the screen. The compounds are tested by disk diffusion assay at a rate of 20 μg/disk. Six active compounds are observed: gliotoxin, moxidectin, thiolutin, antibiotic F42248α, anisomycin and auriothin.

TABLE 1

Standard Fungicide Panel

| Compound | Target |
|---|---|
| amphotericin B | plasma membrane (polyene) |
| cerulenin | fatty acid biosynthesis |
| haloprogin | respiration |
| ketoconazole | ergosterol biosynthesis (lanosterol 14α-demethylase) |
| miconazole | ergosterol biosynthesis (lanosterol 14α-demethylase) |
| diniconazole | ergosterol biosynthesis (lanosterol 14α-demethylase) |
| econazole | ergosterol biosynthesis (lanosterol 14α-demethylase) |
| fenarimole | ergosterol biosynthesis (sterol Δ14 reductase) |
| tridemorph | ergosterol biosynthesis (sterol Δ14 reductase) |
| tolnaftate | ergosterol biosynthesis (squalene mono-oxygenase) |
| U18666A | ergosterol biosynthesis (squalene cyclase) |
| cycloheximide | protein biosynthesis |
| polyoxin D | chitin biosynthesis (cell wall) |
| nikkomycin | chitin biosynthesis (cell wall) |
| nocodazole | microtubule |
| benomyl | microtubule |
| maneb | multi-target |
| metalaxyl | rRNA biosynthesis |
| vinclozolin | lipid peroxidation |
| kanamycin | mitochondria |
| tunicamycin | glycoprotein biosynthesis |
| carboxin | succinate dehydrogenase |
| cyanobutarate | microtubule (plant) |
| antimycin | respiration |
| 5-fluoro-cytosine | nucleotide metabolism |
| glyphosate | herbicide (aromatic amino acid biosynthesis) |
| phosphinothricin | herbicide (glutamine biosynthesis) |
| aminotriazole | herbicide (histidine biosynthesis) |
| sulfometuron methyl | herbicide (branched chain amino acid biosynthesis) |
| pendimethalin | herbicide (microtubule) |

TABLE 2

Standard Antibiotic Panel

| Compound | Compound |
|---|---|
| 4-dedimethylamino-4-methyl-amino-anhydrotetracycline | Actinomycin crude |
| | Actithiazic acid/Mycobacidin |
| Alazopeptin | Amphomycin, Ca |
| Angustmycin | Anisomycin |
| Anthelmycin | Antibiotic A531 |
| Antibiotic A4825 | Antibiotic A7363 |
| Antibiotic A8363 | Antibiotic A9537 |
| Antibiotic AC541, sulfate | Antibiotic AD97 |
| Antibiotic AF283 α | Antibiotic AM31 β & γ |
| Antibiotic AM374 #22 | Antibiotic AN 272 α |
| Antibiotic AO341β HCl | Antibiotic BL580 α |
| Antibiotic BL580 ξ | Antibiotic BM123 α, SO$_4$ |
| Antibiotic BM123 γ HCl | Antibiotic BM782 E |
| Antibiotic BO2964 complex | Antibiotic BO4088 |
| Antibiotic C08078 α | Antibiotic C19004 α |
| Antibiotic E19020 α | Antibiotic E19085 α |
| Antibiotic F42248 α | Antibiotic RA6950 β-B |
| Antibiotic V214X | Antibiotic V214W |
| Antibiotic Z-1220A #3 | Antibiotic F28249 α |
| Antiprotozoin | Ascotoxin |
| Aspartocin, Na salt | Aureothin |
| Aureofungin | Avilamycin |
| Avoparcin sulfate | Azalomycin F |
| Bacitracin | Blasticidin "S" |
| Bottromycin | Cabomycin |
| Chloramphenical | Citrinin |
| Clavacin/Patulin | Declomycin HCl |
| Dermostatin | Destomycin A |
| Etamycin, Na salt | Flavofungin |
| Folimycin | Frenolicin (AC860 α) |
| Fusarinic acid | Geldamycin |
| Gibberellic acid | Gliotoxin |
| Griseofulvin, 5OH | Hamycin |
| Hygromycin A | Isoquinocycline HCl(AA575) |
| Lemonomycin | Leucomycin |
| Levomycin | Lincomycin HCl |
| Mocimycin | Monazomycin |
| Monicamycin | Moxidectin |
| Mycolutein | Mycophenolic acid |
| Mycorhodin | Naramycin B |
| Neohumidin | Neomycin SO$_4$ |
| Netropsin, HCl | Neutramcin |
| Nonactin (AE409 γ) | Nosiheptide |
| Nucleocidin | Nybomycin |
| Nystatin | Paromomycin, sulfate |
| Pentamycin | Phenazine α-COOH |
| Picromycin | Piramicin/Tennectin |
| Polymyxin-B-sulfate | Protomycin/Streptimidone |
| Puromycin Aminonucleoside | Puromycin HCl |
| Pyrenophorin | Ramulosin |
| Relomucin, LL-AM684 β | Ristocetin |
| Rugulosin | Sparsomycin |
| Streptogramin/Vertimycin | Streptomycin SO$_4$ |
| Sulfocidin | Tennecetin |
| Tetrahydro spiramycin base | Thioaurin |
| Thiolutin | Trichomycin |
| Tubercidin | Tylosin, tartrate |
| Usnic acid | Valinomycin/Miticide |
| Vancomycin HCl | Viomycin, sulfate |

Using a qualitative scoring system based on zone size differences observed in the assay, 28 weak, 10 moderate and 4 strong actives are obtained in a screening of about 7000 synthetic compounds using the method.

EXAMPLE 2

This example describes the cloning and sequencing of the *Saccharomyces cerevisiae* gene encoding sterol Δ14 reductase, and the preparation of a strain transformed with a plasmid containing the gene for use in the secondary screen described in the next example. The gene is isolated and cloned by selecting strains carrying sequences on a 2 μ based vector for resistance to the morpholine fungicide, fenpropimorph, to obtain a plasmid which is shown to carry the structural gene based upon the phenotype of gene disruption strains.

Isolation and characterization of morpholine resistance plasmids.

Morpholine and structurally related piperidine fungicides reportedly inhibit sterol Δ14 reductase and sterol Δ8–Δ7 isomerase (Baloch, R. and Mercer, I., *Phytochemistry* 26: 663–668 (1987)). The growth of *S. cerevisiae* strain Y294, genotype MATα, leu2-3,112, ura3-52, his3Δ, trp1, Gal⁺ (Brugge, J. S., et al., *Mol. Cell. Biol.* 7:2180–2187 (1987)), in SD medium supplemented with leucine, tryptophan, uracil and histidine is inhibited by 20 μg/ml of the morpholine fungicide fenpropimorph and 50 μg/ml of the morpholine fungicide tridemorph. Fenpropimorph is used for subsequent selection experiments because of its slightly greater potency.

When Y294 cells are plated onto 20 μg/ml of fenpropimorph in SD media supplemented with leucine, tryptophan, uracil and histidine, spontaneous mutants are recovered at the rate of ~1 per $2.5 \times 10^6$ plated cells. When a library of *S. cerevisiae* sequences in the multicopy vector YEp13 (Nasmyth, K. A., and Tatchell, K., *Cell* 19: 753–764 (1980)) is introduced into strain Y294 and cells are plated on SD media supplemented with tryptophan, uracil, histidine and fenpropimorph, resistant colonies appeared at the rate of ~1 per $10^4$, suggesting that resistance is produced by library plasmids in some of the colonies. Plasmids are cured from randomly selected resistant colonies by growing the cells in non-selective rich YEPD media and retesting for fenpropimorph resistance. In 13 strains, the plasmid cured derivative shows sensitivity to 20 μg/ml fenpropimorph while the original plasmid carrying strain retested as fenpropimorph-resistant.

DNA is isolated from these 13 strains and plasmid DNA is recovered by *E. coli* transformation. Five different types of plasmid DNA are identified following an examination of restriction enzyme digestion patterns using standard methods (FIG. 1). Seven strains carry one plasmid type, pML99, which has an insert of approximately 5.5 kb. Two additional strains carry a second plasmid type, pML-100, which has an insert of approximately 5.6 kb. A third plasmid type, pML101, is found in two strains and carries an insert of approximately 5.5 kb. Two additional plasmid types are each recovered from a single strain and named pML102 (~7.5 kb insert) and pML103 (~5.1 kb insert). One representative plasmid of each type is selected and subjected to extensive restriction enzyme analysis, which indicates that the insert from plasmid pML101 is contained within the insert from pML102 so that a total of four unique sequences are recovered in this selection. Restriction enzyme digestion maps of the four different insert sequences are shown in FIG. 1.

A panel of fungicides representing a variety of chemical structures and mechanisms of action listed in Table 1 is tested by disk diffusion assay against strains carrying each of these plasmids in a YEp13 vector control. All five strains show similar levels of sensitivity to all of the tested compounds with the exception of the morpholines, fenpropimorph and tridemorph, and azasterol. These compounds are less active on the strains carrying the four plasmids recovered by selection for fenpropimorph resistance. Consistent with agar dilution sensitivity results, fenpropimorph is more active by disk diffusion than tridemorph. These results suggest that the cloned sequences encode functions specific to the activity of morpholines and related compounds and do not carry genes which produce general fungicide resistance, e.g., by altering cell permeability.

The library employed for the selection is prepared using DNA isolated from strain AB320 (genotype HO, ade2-1, lys2-1, trp5-2, leu2-1, can1-100, ura3-1 and/or ura1-1, met4-1, Nasmyth and Tatchell, cited above). When tested, strain AB320 is found to be slightly more sensitive to fenpropimorph than strain Y294, suggesting that the cloned sequences are likely to be producing resistance as the result of gene dosage effects.

Morpholine resistance in strains transformed with multi-copy ERG2 (sterol Δ8–Δ7 isomerase) plasmids.

One gene that would be expected to produce morpholine resistance at high copy is ERG2, which encodes a reported morpholine target, Δ8–Δ7 isomerase. This gene was recently cloned by the complementation of a polyene resistance mutation (Ashman, cited above). The published ERG2 restriction map is different from the restriction maps of the four sequences recovered by morpholine resistance selection. Since it is possible that the ERG2 sequence is missed in the morpholine resistance screen, this gene is introduced into *S. cerevisiae* strain Y294 on the 2 μ based plasmid, pML104, constructed by subcloning the ERG2 gene on a 2.1 kb HindIII fragment from plasmid PIU406 (Ashman, et al., cited above) into the HindIII site of plasmid YEp351. This strain shows no increase in fenpropimorph resistance relative to YEp351-transformed control strain. Plasmid pML104 does, however, produce nystatin sensitivity when introduced into the erg2 mutant strain WAO (Ashman, et al., cited above), demonstrating that plasmid pML104 carries a functional ERG2 gene. Sterol Δ8–Δ7 isomerase may not overexpress when present on a 2 μ based, multi-copy plasmid, or the enzyme may not be a morpholine target in *S. cerevisiae*.

Characterization of fenpropimorph resistance plasmid pML100.

The four fenpropimorph resistance plasmids pML99, pML100, pML101, and pML103 are transformed into three ergosterol pathway mutant strains, erg2 (denoted WAO, genotype MATa, his7-2, leu2-3,112, ura3-52, erg2-3, Ashman, et al., cited above); erg3 (denoted XML39-1d, genotype MATa, leu2-3,112, erg3-2); and erg6 (denoted XML40-1c, genotype MATα, leu2-3,112, gal2, erg6-5). Morpholine sensitivity is determined by disk diffusion assay on appropriately supplemented SD medium using tridemorph and fenpropimorph. A zone size difference of greater than 3 mm performed in duplicate is recorded as resistance. The ergosterol pathway mutant strains vary in absolute level of morpholine sensitivity, and all resistance and sensitivity determinations are reported relative to vector (YEp-13)-transformed control strains. The results are tabulated in Table 3. Only plasmid pML100 transformants are consistently fenpropimorph-resistant in all genetic backgrounds, but the other plasmics are useful in screening methods.

TABLE 3

Plasmid Phenotype in Ergosterol Pathway Mutant Strains

| Strain | Ergosterol Genotype | Plasmid | Morpholine Resistance |
|---|---|---|---|
| Y294 | ERG+ | YEp13 | − |
| Y294 | ERG+ | pML99 | + |
| Y294 | ERG+ | pML100 | + |
| Y294 | ERG+ | pML101 | + |
| Y294 | ERG+ | pML103 | + |
| WAO | erg2 | YEp13 | − |
| WAO | erg2 | pML99 | − |
| WAO | erg2 | pML100 | + |

TABLE 3-continued

Plasmid Phenotype in Ergosterol Pathway Mutant Strains

| Strain | Ergosterol Genotype | Plasmid | Morpholine Resistance |
| --- | --- | --- | --- |
| WAO | erg2 | pML101 | − |
| WAO | erg2 | pML103 | − |
| XML39-1d | erg3 | YEp13 | − |
| XML39-1d | erg3 | pML99 | + |
| XML39-1d | erg3 | pML100 | + |
| XML39-1d | erg3 | pML101 | − |
| XML39-1d | erg3 | pML103 | +/−* |
| XML40-1c | erg6 | YEp13 | − |
| XML40-1c | erg6 | pML99 | + |
| XML40-1c | erg6 | pML100 | + |
| XML40-1c | erg6 | pML101 | − |
| XML40-1c | erg6 | pML103 | +/−* |

*—Resistance was observed with fenpropimorph but not tridemorph.

Resistance is also seen with other morpholine antifungals (tridemorph and fenpropidin) and azasterol, all of which are reported to be inhibitors of sterol Δ14 reductase. However, no increase is seen to a variety of other fungicides which are not sterol Δ14 reductase inhibitors. Since resistance occurs only to sterol Δ14 reductase inhibitors and is seen for such inhibitors from two different chemical classes, it is likely that pML100 encodes a function specific to sterol Δ14 reductase activity.

Figure 2:
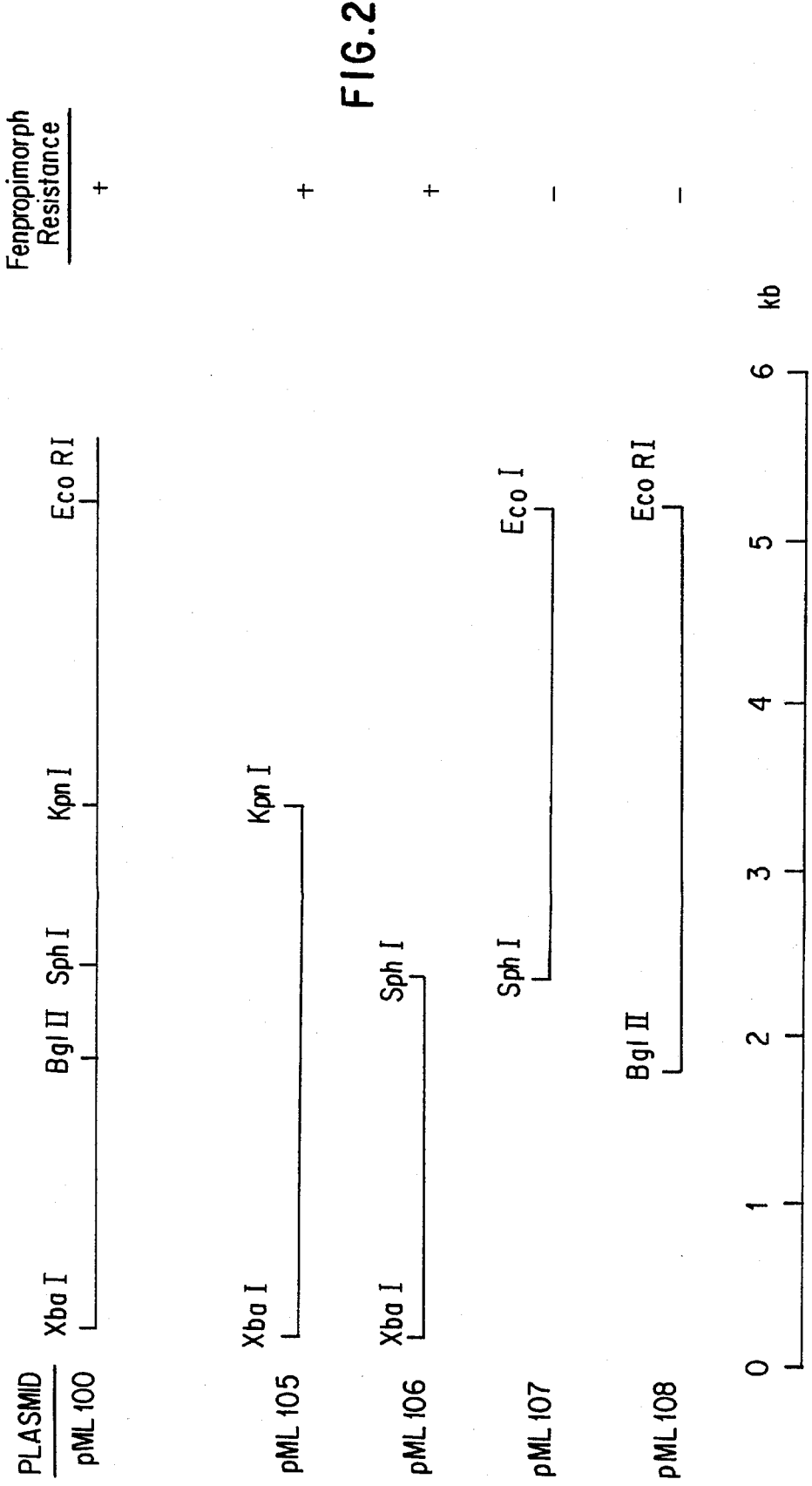
FIG. 2 shows fenpropimorph resistance of subclones of pML100, a plasmid containing the cloned sterol Δ14 reductase gene.

Subclones of the pML100 insert are prepared in the yeast shuttle vector YEp352, transformed into yeast strain Y294, and tested for fenpropimorph resistance. As shown in FIG. 2, the fenpropimorph resistance region is limited to a 2.5 kb SphI/XbaI fragment located near one side of the insert/vector border.

Plasmid pML106, which contains this fragment in vector YEp352, is cleaved with BglII, which cuts once at a site near the middle of the SphI/XbaI fragment. A 3.0 kb BglII fragment containing the S. cerevisiae LEU2 gene is isolated from plasmid YEp13 and ligated into this BglII cite, producing plasmid pML108. The disrupted 5.5 kb SphI/XbaI fragment containing the LEU2 gene is isolated from plasmid pML108 and used to transform S. cerevisiae strain YPH501 to leucine prototrophy. Transformants in which the 5.5 kb SphI/XbaI fragment replaced the 2.5 kb SphI/XbaI fragment in one chromosomal homologue are identified by Southern analysis.

Tetrads from one such transformant (strain YPH501-2-1) are dissected and the spores germinated under anaerobic conditions on YEPD medium supplemented with Tween® 80 (500 μg/ml) and ergosterol (20 μg/ml). Strain YPH501-2-1 shows low (approximately 50%) spore viability, and no tetrads are recovered. This is found to be a property of strain YPH501 which showed a similar low level of spore viability when spores from the host strain are germinated anaerobically. By random spore analysis, 15 of 32 segregants are both Leu⁺ and obligate anaerobes, suggesting that the disruption has produced a genetic lesion in sterol biosynthesis. (The remaining 17 segregants are Leu⁻ and grow aerobically.)

One such obligate anaerobe segregant, denoted YPH501-2-1-3C, is analyzed for sterol content. The strain is grown anaerobically on YEPD medium containing ergosterol (5 μg/ml) to facilitate sterol uptake. After one day, the cells are harvested, washed in saline, resuspended in YEPD medium with no added sterol and grown for an additional 2 days to deplete cellular sterol. After 3 days, sterols are extracted from stationary phase yeast cells into n-heptane and analyzed by ultraviolet (UV) between 200 and 300 nm, gas chromatography (GC) and gas chromatography/mass spectrometry (GC-MS). GC-MC analyses are performed on a Hewlett Packard (HP) 5980 instrument using a 30 meter ×0.25 mm HP-5 column with a 25 micron film thickness. The column temperature is programmed from 280° C. to 300° C. with the initial temperature maintained for 2 minutes and increased at 3° C./minute. The final temperature is held for 6 minutes. The mass spectrometer is operated in the electron impact ionization mode at 70 eV. High pressure liquid chromatography (HPLC) analyses are performed using a reverse phase column (2.1×100 mm) packed with 5 micron spherical C18 bonded silica. Sterol samples are dissolved in a methanol:ethyl acetate (1:1) mixture and eluted from HPLC with 95% acetonitrile in water at 1 ml/minute. The detection wavelength is 270 nm.

UV analysis demonstrates a 250 nm broad peak indicative of a sterol containing a conjugated double bond system involving C-8(9) and C-14(15). GC analyses indicate a major peak with the relative retention time of 1.30 consistent with ignosterol (ergosta-8,14-dien-3β-ol, molecular weight 398), the sterol Δ14 reductase substrate. GC-MS analysis confirms that the major sterol accumulating in this disrupted strain is ignosterol. Small amounts of lanosterol, approximately 5%, are also observed, consistent with a block in the sterol pathway downstream of lanosterol and affecting the reduction of the C-14 double bond. The accumulation of ignosterol indicates a genetic lesion in sterol Δ14 reductase activity.

DNA sequence analysis of plasmid pML100.

The DNA sequence of the 2.5 kb SphI/XbaI fragment of plasmid pML100 is set out in the Sequence Listing section hereinafter as SEQ ID NO 1 and more particularly described in copending U.S. application Ser. No. 08/107,347 filed concurrently with this application and incorporated in its entirety by reference. An open reading frame of 1314 base pairs is identified starting at an ATG codon at position 419 within the sequence. No other open reading frame of significant size is present within this fragment. Up-stream of this ATG codon is an AT-rich sequence (66%), typical of many functionally expressed S. cerevisiae genes. This open reading frame encodes a 438 amino acid, 50.5 kilodalton basic (pI=9.2), presumptive integral membrane protein which, based upon hydropathy analysis using a computer program that progressively evaluates the hydrophilicity and hydrophobicity of a protein along its amino acid sequence (Kyte, J., and Doolittle, R. F., J. Mol. Biol. 157: 105–132 (1982)), contains 8 or 9 putative transmembrane domains.

Other investigators report that selection for fenpropidin or fenpropimorph resistance in other S. cerevisiae strains produced plasmids exhibiting properties similar to pML100 (Lorenz and Parks, and Marcireau, C., et al., cited above).

EXAMPLE 3

Compounds found to be actives in the primary screen of Example 1 are assayed using transformed strain Y294 (pML100) of Example 2 in a secondary screen.

Synthetic Dropout Media is first prepared by combining

| | |
| --- | --- |
| Dropout Agar Base (DOBA, Bio-101) | 44 g |
| CSM-LEU (Bio-101) | 0.8 g |
| Distilled Water | 1000 ml | and autoclaving 15 minutes at 20 pounds pressure.

Overnight cultures of Y294(pML100) and Y294(YEp13) are grown overnight in liquid synthetic dropout media (without agar) shaken at 30° C. The culture is grown to an OD$_{600}$ of ~2.5. One part of culture inoculum is added to 100 parts test media.

Test medium is prepared by combining 1 part Y294 (pML100) or Y294(YEp13) into warm synthetic dropout media. Pour plates for each culture, prepare test samples in duplicate and place each test sample on a Y294(pML100)

plate and a Y294(YEp13) plate. A ¼" disc containing 100 µg of fenpropimorph is used as a positive control. The plates are incubated at 30° C. for two days and then examined to compare activity on the two strains. Actives produce a smaller zone on the Y294(pML100) plate than on the Y294 (YEp13) plate.

Morpholines are detected in this assay at 12.5 µg/disk for fenpropimorph and fenpropidin and 50 µg/disk for tridimorph. As a result, actives are generally concentrated 2500-fold prior to testing in the secondary screen. The same panel of fungicides set out in Table 1 and antibiotics set out in Table 2 (Example 1) are tested in the secondary screen. All of the actives from the primary screen with undesired mechanisms of action are inactive in the secondary assay. All of the active compounds from the panel of 7000 compounds tested in the primary screen of Example 1 were tested, and only one is active in the secondary screen. Thus, the two screens, when carried out together, are highly sensitive and specific for the detection of sterol Δ14 reductase inhibitors.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

BIBLIOGRAPHY

Ashman, W. H., et al., *Lipids* 26: 628–632 (1991).
Baloch, R. and Mercer, I., *Phytochemistry* 26: 663–668 (1987).
Brugge, J. S., et al., *Mol. Cell. Biol.* 7:2180–2187 (1987).
Ellis, S. W., et al., *J. Gen. Micro.* 137: 267–272 (1992).
Grindle, M., and Farrow, R., *Mol. Gen. Genet.* 165: 305–308 (1978).
Kyte, J., and Doolittle, R. F., *J. Mol. Biol.* 157: 105–132 (1982).
Lorenz, T., and Parks, L. W., *DNA and Cell Biol.* 11: 685–692 (1992).
Marcireau, C., et al., *Curr. Genet.* 22: 267–272 (1992).
Mercer, E. I., *Biochem. Soc. Trans.* 19: 788–308 (1991).
Nasmyth, K. A., and Tatchell, K., *Cell* 19: 753–764 (1980).
Paltauf, F., et al., in Jones, E. W., et al., eds., *The Molecular and Cellular Biology of the Yeast Saccharomyces, Gene Expression,* Cold Spring Harbor Laboratory Press, 1992, pages 415, 418–420, 424–428 and 434–437.

We claim:

1. A method for screening for the presence or absence of sterol Δ14 reductase inhibition by a test sample, said method comprising:

(a) adding the test sample to a culture of a *Neurospora crassa* strain having an erg-3 mutation;

(b) adding the test sample to a second culture of a *Neurospora crassa* strain having an erg-1 mutation;

(c) incubating the cultures for such time under such conditions sufficient to observe fungal cell growth in corresponding cultures containing no test sample;

(d) comparing the extent of growth inhibition in the culture containing the erg-3 mutation with the extent of growth inhibition in the culture containing the erg-1 mutant; and (e) determining the presence of sterol biosynthesis inhibition by observation that growth inhibition in the erg-3 culture exceeds growth inhibition in the erg-1 culture.

2. A method according to claim 1 further comprising, as a control, adding a known inhibitor of sterol Δ14 reductase to both *N. crassa* strains prior to incubation.

3. A method according to claim 2 wherein said control is selected from the group consisting of tridemorph, fenpropimorph, fenpropidin, and azasterol.

4. A method according to claim 3 wherein said control is tridemorph.

5. A method according to claim 1 wherein the cultures containing test samples are solidified cultures and test samples are added to the cultures on a disk or in a well.

6. A method for screening for the presence or absence of sterol Δ14 reductase inhibition by a test sample, said method comprising:

(a) adding the test sample to a culture of a *Saccharomyces cerevisiae* strain into which has been introduced a gene encoding sterol Δ14 reductase;

(b) adding the test sample to a culture of a corresponding *Saccharomyces cerevisiae* strain which does not have an introduced sterol Δ14 reductase gene;

(c) incubating the test sample in the cultures for such time under such conditions sufficient to observe yeast cell growth in corresponding cultures containing no test sample;

(d) comparing the extent of growth inhibition in the culture having the reductase gene with the extent of growth inhibition in the corresponding culture having no introduced gene; and (e) determining the presence of sterol Δ14 reductase inhibition by observation that growth inhibition in the corresponding culture having no introduced reductase gene exceeds growth inhibition in the culture having the introduced reductase gene.

7. A method according to claim 6 further comprising, as a control, adding a known inhibitor of sterol Δ14 reductase to both yeast strains prior to incubation.

8. A method according to claim 7 wherein the known inhibitor of sterol Δ14 reductase is selected from the group consisting of fenpropimorph, fenpropidin, tridimorph, and azasterol.

9. A method according to claim 8 wherein the known inhibitor is fenpropimorph.

10. A method according to claim 6 wherein the culture of a *Saccharomyces cerevisiae* strain is a *S. cerevisiae* strain into which has been introduced a gene encoding sterol Δ14 reductase at sufficient copy number to overexpress the enzyme in an amount greater than a *S. cerevisiae* strain which has not been introduced with said gene.

11. A method according to claim 10 wherein the strain is Y294 (pML100).

12. A method according to claim 11 wherein the culture of a corresponding *Saccharomyces cerevisiae* strain which does not have an introduced sterol Δ14 reductase gene is Y294-(YEp13).

13. A method according to claim 6 wherein the cultures containing test samples are solidified cultures and test samples are added to the cultures on a disk or in a well.

14. A method according to claim 6 wherein said *S. cerevisiae* strain into which has been introduced a sterol Δ14 reductase gene is a strain transformed with plasmid pML100.

15. A method for screening for the presence or absence of sterol Δ14 reductase inhibition by a test sample, which comprises:

(a) first screening the test sample in a primary screen comprising the steps of:
(i) adding the test sample to a culture of a *Neurospora crassa* strain having an erg-3 mutation;
(ii) adding the test sample to a second culture of a *Neurospora crassa* strain having an erg-1 mutation;
(iii) incubating the test samples in the cultures for such time under such conditions sufficient to observe fungal cell growth in corresponding cultures containing no test sample;
(iv) comparing the extent of growth inhibition in the culture containing the erg-3 mutation with the extent of growth inhibition in the culture containing the erg-1 mutant; and
(v) identifying a positive test sample by observing that growth inhibition in the erg-3 culture containing the test sample exceeds growth inhibition in the erg-1 culture containing the test sample; followed by (b) screening said positive test sample in a secondary screen comprising the steps of:
(vi) adding a positive test sample from the primary screen to a culture of a *Saccharomyces cerevisiae* strain into which has been introduced at high copy a gene encoding sterol Δ14 reductase;
(vii) adding the positive test sample to a culture of a corresponding *Saccharomyces cerevisiae* strain which does not have an introduced sterol Δ14 reductase gene;
(viii) incubating the samples in the cultures for such time under such conditions sufficient to observe yeast cell growth in corresponding cultures containing no test sample;
(ix) comparing the extent of growth inhibition in the culture having the reductase gene with the extent of growth inhibition in the corresponding culture having no introduced gene; and
(x) determining the presence of sterol Δ14 reductase inhibition by observation that inhibition in the culture having no introduced reductase gene exceeds growth inhibition in the corresponding culture having the introduced reductase gene.

16. A method according to claim 15 further comprising, as a control, adding a known inhibitor of sterol Δ14 reductase to both *N. crassa* and both *S. cerevisiae* strains prior to incubation during the respective primary and secondary screens.

17. A method according to claim 16 wherein the control in the *N. crassa* incubations is tridemorph and the control in the *S. cerevisiae* incubations is fenpropimorph.

18. A method according to claim 15 wherein the *N. crassa* and *S. cerevisiae* cultures containing test samples are solidified cultures and test samples are added to the cultures on a disk or in a well, and growth inhibition is determined by visual inspection.

19. A method according to claim 15 wherein the positive test sample in the primary screen is concentrated before testing with the secondary screen.

20. A plasmid containing, as an insert, the nucleotide sequence of SEQ ID NO. 1.

21. A plasmid according to claim 20 comprising pML100.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
      ( A ) LENGTH: 2528 bases
      ( B ) TYPE: nucleic acid
      ( C ) STRANDEDNESS: double
      ( D ) TOPOLOGY: linear ( i i ) MOLECULE TYPE:
      ( A ) DESCRIPTION: DNA encoding a polypeptide ( v ) FRAGMENT TYPE: entire sequence ( v i ) IMMEDIATE SOURCE: Saccharomyces cerevisiae
         clone ( i x ) FEATURE:
      ( D ) OTHER INFORMATION: sterol delta 14 reductase gene,
         translated polypeptide and flanking DNA ( x i ) SEQUENCE DESCRIPTION: SEQ ID NO:1:

```
ATATATATAT  ACCTCTTGCC  AGCAACAGGC  CAGTTATAAG  TTAAAATTAA              50

TATGTGACGC  ACTTCTGAAA  CAGTATTGAA  ACAGTATTGA  AACATATGTA             100

TTACCCGGAC  TCTGCATGCT  CTGTCGTTCA  TTTTATTTTC  ACCTAAACGA             150

AAATCCCGTG  AAAAAAATTT  ATATCGCCTT  TCGCTCTTTT  GTATGTAGGC             200

ATCATCGGAA  ATTTGCATTG  TGTGAAGGTT  GTGCATATAA  AGGGTTTTGC             250

ATAACGGACG  TTTTTCACGT  ACTCCGTCTG  AGCATCAAGT  GAGGCTTGAG             300

TTTACGTTTG  TTTTTAATAA  TCAGTTTTCA  TTCTACTATT  TTCTTGCGCA             350

ATTGCTTATC  AGATAGACCT  TGTAAACAGC  ATAGGAGTAA  AGACAAATTC             400

GGTGTAGAGA  ATAAAAGG  ATG  GTA  TCA  GCT  TTG  AAT  CCC  AGA  ACT  ACA  GAG   451
```

|  |  |  |  | Met | Val | Ser | Ala | Leu | Asn | Pro | Arg | Thr | Thr | Glu |  |
|--|--|--|--|--|--|--|--|--|--|--|--|--|--|--|--|
|  |  |  |  |  |  |  |  | 5 |  |  |  |  |  | 10 |  |

| TTT | GAA | TTT | GGT | GGG | CTG | ATT | GGT | GCC | TTA | GGC | ATC | AGC | ATA | GGG | 496 |
|-----|-----|-----|-----|-----|-----|-----|-----|-----|-----|-----|-----|-----|-----|-----|-----|
| Phe | Glu | Phe | Gly | Gly | Leu | Ile | Gly | Ala | Leu | Gly | Ile | Ser | Ile | Gly |  |
|     |     |     |     | 15  |     |     |     |     | 20  |     |     |     |     | 25  |  |

| CTG | CCT | GTT | TTC | ACT | ATC | ATC | TTG | AAT | CAA | ATG | ATA | AGG | CCC | GAT | 541 |
| Leu | Pro | Val | Phe | Thr | Ile | Ile | Leu | Asn | Gln | Met | Ile | Arg | Pro | Asp |  |
|     |     |     |     | 30  |     |     |     |     | 35  |     |     |     |     | 40  |  |

| TAT | TTT | ATT | AAG | GGA | TTT | TTC | CAG | AAT | TTC | GAT | ATA | GTT | GAG | CTT | 586 |
| Tyr | Phe | Ile | Lys | Gly | Phe | Phe | Gln | Asn | Phe | Asp | Ile | Val | Glu | Leu |  |
|     |     |     |     | 45  |     |     |     |     | 50  |     |     |     |     | 55  |  |

| TGG | AAC | GGT | ATC | AAG | CCA | TTG | CGC | TAC | TAT | CTG | GGC | AAT | CGT | GAA | 631 |
| Trp | Asn | Gly | Ile | Lys | Pro | Leu | Arg | Tyr | Tyr | Leu | Gly | Asn | Arg | Glu |  |
|     |     |     |     | 60  |     |     |     |     | 65  |     |     |     |     | 70  |  |

| TTA | TGG | ACT | GTC | TAT | TGC | CTG | TGG | TAT | GGA | ATA | CTG | GCA | GTT | TTG | 676 |
| Leu | Trp | Thr | Val | Tyr | Cys | Leu | Trp | Tyr | Gly | Ile | Leu | Ala | Val | Leu |  |
|     |     |     |     | 75  |     |     |     |     | 80  |     |     |     |     | 85  |  |

| GAC | GTC | ATT | TTA | CCG | GGC | AGA | GTC | ATG | AAG | GGT | GTT | CAG | TTA | AGG | 721 |
| Asp | Val | Ile | Leu | Pro | Gly | Arg | Val | Met | Lys | Gly | Val | Gln | Leu | Arg |  |
|     |     |     |     | 90  |     |     |     |     | 95  |     |     |     |     | 100 |  |

| GAT | GGT | TCG | AAG | CTT | TCG | TAT | AAG | ATC | AAT | GGA | ATT | GCC | ATG | TCT | 766 |
| Asp | Gly | Ser | Lys | Leu | Ser | Tyr | Lys | Ile | Asn | Gly | Ile | Ala | Met | Ser |  |
|     |     |     |     | 105 |     |     |     |     | 110 |     |     |     |     | 115 |  |

| ACA | ACT | TTG | GTC | TTA | GTT | TTG | GCT | ATC | AGA | TGG | AAA | TTG | ACT | GAT | 811 |
| Thr | Thr | Leu | Val | Leu | Val | Leu | Ala | Ile | Arg | Trp | Lys | Leu | Thr | Asp |  |
|     |     |     |     | 120 |     |     |     |     | 125 |     |     |     |     | 130 |  |

| GGA | CAA | TTG | CCT | GAA | TTG | CAA | TAT | CTG | TAT | GAA | AAT | CAC | GTT | AGT | 856 |
| Gly | Gln | Leu | Pro | Glu | Leu | Gln | Tyr | Leu | Tyr | Glu | Asn | His | Val | Ser |  |
|     |     |     |     | 135 |     |     |     |     | 140 |     |     |     |     | 145 |  |

| TTA | TGC | ATA | ATA | TCT | ATT | TTG | TTT | TCG | TTC | TTT | TTG | GCG | ACG | TAC | 901 |
| Leu | Cys | Ile | Ile | Ser | Ile | Leu | Phe | Ser | Phe | Phe | Leu | Ala | Thr | Tyr |  |
|     |     |     |     | 150 |     |     |     |     | 155 |     |     |     |     | 160 |  |

| TGC | TAT | GTT | GCC | AGC | TTC | ATA | CCA | TTG | ATC | TTC | AAG | AAA | AAT | GGT | 946 |
| Cys | Tyr | Val | Ala | Ser | Phe | Ile | Pro | Leu | Ile | Phe | Lys | Lys | Asn | Gly |  |
|     |     |     |     | 165 |     |     |     |     | 170 |     |     |     |     | 175 |  |

| AAT | GGC | AAA | AGG | GAA | AAG | ATC | TTA | GCA | CTA | GGT | GGA | AAT | TCA | GGA | 991 |
| Asn | Gly | Lys | Arg | Glu | Lys | Ile | Leu | Ala | Leu | Gly | Gly | Asn | Ser | Gly |  |
|     |     |     |     | 180 |     |     |     |     | 185 |     |     |     |     | 190 |  |

| AAC | ATC | ATT | TAC | GAT | TGG | TTT | ATT | GGT | AGA | GAA | CTG | AAC | CCT | CGT | 1036 |
| Asn | Ile | Ile | Tyr | Asp | Trp | Phe | Ile | Gly | Arg | Glu | Leu | Asn | Pro | Arg |  |
|     |     |     |     | 195 |     |     |     |     | 200 |     |     |     |     | 205 |  |

| CTC | GGC | CCA | TTA | GAT | ATC | AAG | ATG | TTT | TCA | GAG | TTG | AGA | CCC | GGC | 1081 |
| Leu | Gly | Pro | Leu | Asp | Ile | Lys | Met | Phe | Ser | Glu | Leu | Arg | Pro | Gly |  |
|     |     |     |     | 210 |     |     |     |     | 215 |     |     |     |     | 220 |  |

| ATG | TTG | TTA | TGG | TTA | CTG | ATC | AAT | CTT | TCC | TGT | CTG | CAT | CAC | CAT | 1126 |
| Met | Leu | Leu | Trp | Leu | Leu | Ile | Asn | Leu | Ser | Cys | Leu | His | His | His |  |
|     |     |     |     | 225 |     |     |     |     | 230 |     |     |     |     | 235 |  |

| TAC | CTG | AAG | ACT | GGT | AAA | ATC | AAC | GAT | GCA | TTG | GTC | TTG | GTT | AAT | 1171 |
| Tyr | Leu | Lys | Thr | Gly | Lys | Ile | Asn | Asp | Ala | Leu | Val | Leu | Val | Asn |  |
|     |     |     |     | 240 |     |     |     |     | 245 |     |     |     |     | 250 |  |

| TTC | TCG | CAA | GGA | TTT | TAC | ATT | TTC | GAT | GGA | GTA | CTA | AAC | GAG | GAA | 1216 |
| Phe | Ser | Gln | Gly | Phe | Tyr | Ile | Phe | Asp | Gly | Val | Leu | Asn | Glu | Glu |  |
|     |     |     |     | 255 |     |     |     |     | 260 |     |     |     |     | 265 |  |

| GGT | GTA | TTA | ACC | ATG | ATG | GAT | ATC | ACT | ACA | GAT | GGG | TTT | GGT | TTC | 1261 |
| Gly | Val | Leu | Thr | Met | Met | Asp | Ile | Thr | Thr | Asp | Gly | Phe | Gly | Phe |  |
|     |     |     |     | 270 |     |     |     |     | 275 |     |     |     |     | 280 |  |

| ATG | CTA | GCG | TTT | GGT | GAC | TTA | AGT | TTA | GTT | CCA | TTC | ACC | TAC | TCA | 1306 |
| Met | Leu | Ala | Phe | Gly | Asp | Leu | Ser | Leu | Val | Pro | Phe | Thr | Tyr | Ser |  |
|     |     |     |     | 285 |     |     |     |     | 290 |     |     |     |     | 295 |  |

| TTA | CAA | GCG | CGT | TAC | TTG | AGT | GTT | TCC | CCT | GTG | AAA | TTG | GGA | TGG | 1351 |

| | | | | | | | | | | | | | | |
|---|---|---|---|---|---|---|---|---|---|---|---|---|---|---|
| Leu | Gln | Ala | Arg | Tyr<br>300 | Leu | Ser | Val | Ser | Pro<br>305 | Val | Glu | Leu | Gly | Trp<br>310 |

```
GTG AAA GTT GTC GGT ATA TTA GCC ATA ATG TTT TTG GGT TTC CAC      1396
Val Lys Val Val Gly Ile Leu Ala Ile Met Phe Leu Gly Phe His
                315                 320                 325

ATC TTC CAC TCG GCA AAT AAG CAA AAA TCT GAG TTT AGA CAA GGT      1441
Ile Phe His Ser Ala Asn Lys Gln Lys Ser Glu Phe Arg Gln Gly
                330                 335                 340

AAA TTA GAA AAT CTA AAA AGT ATT CAG ACA AAG CGT GGT ACA AAG      1486
Lys Leu Glu Asn Leu Lys Ser Ile Gln Thr Lys Arg Gly Thr Lys
                345                 350                 355

TTA TTA TGT GAC GGG TGG TGG GCT AAA TCA CAG CAT ATC AAT TAC      1531
Leu Leu Cys Asp Gly Trp Trp Ala Lys Ser Gln His Ile Asn Tyr
                360                 365                 370

TTT GGC GAT TGG CTG ATT TCA TTA AGT TGG TGT TTG GCC ACC TGG      1576
Phe Gly Asp Trp Leu Ile Ser Leu Ser Trp Cys Leu Ala Thr Trp
                375                 380                 385

TTC CAA ACT CCC TTG ACA TAT TAC TAC TCG TTG TAC TTC GCC ACG      1621
Phe Gln Thr Pro Leu Thr Tyr Tyr Tyr Ser Leu Tyr Phe Ala Thr
                390                 395                 400

TTG TTA TTA CAC CGT CAA CAA CGT GAT GAG CAC AAG TGC CGC CTG      1666
Leu Leu Leu His Arg Gln Gln Arg Asp Glu His Lys Cys Arg Leu
                405                 410                 415

AAA TAT GGC GAA AAT TGG GAA GAA TAC GAA AGA AAA GTT CCT TAC      1711
Lys Tyr Gly Glu Asn Trp Glu Glu Tyr Glu Arg Lys Val Pro Tyr
                420                 425                 430

AAG ATC ATT CCA TAT GTT TAT TAAGTTTTTC TACCACTGCT ATTTCTTCA      1762
Lys Ile Ile Pro Tyr Val Tyr
                435

TTATCTATGT ATGTGTGTAT ACATGTTATG TATTGGGTGA GTATGAGGAA           1812

GAAGAAGAAT AACAATTGAA AACGCTGGAA AAATTAAAAG GGGTGGCGGT           1862

CTATCTATGC AACGCTCCCC TTTTCGTTAC ATGAACACAT CAAACTTGTA           1912

TATCCTTTGA GTGTTCTTTA ATCAAGTCAT CTTGGTATTT TAGTAGCGTT           1962

TCCACTACTT TAGGGACAAA TTCAGACCTA ACCAATCCAT CAAAAGCATC           2012

AAACCCTTGC GACAAAATCG GAATATCAGA CTCGCCATGC ATAAACTCTG           2062

GAATTTCTAG TTTCCCGTCC GCAAGTATGC CGTCATCATC CTCGTCGTCC           2112

TTATTAGTAT CCAAATTTGT CACTTTGACG TTCATCGACA ACTGTAAGTC           2162

AAAGTAGCAA ATCGCCTTGC CCTTCCTTTG AGATACGTTG GAGTCACCGG           2212

TGATGCTACT CACCTGGGTT AACTCAATTT TGCTCTTCCC ATCAGAGGAA           2262

ACAGTGGACA AACTCGTTAA TTTACCGTTC AAGTAGTCCT TAGACCAAGG           2312

TAAGGTGTTT TTATCCACCC AATGCCAGTT ATTTGGATTC AAGACAACCA           2362

TATTTTATCG TAAATGTGTT GTAACTTTCC GATCGTTTCA AACTTTAGTA           2412

GTAGTTTGAT GATTTTGTCC AAAAAGTATT TGCTTAAATT TCAGCTTTTT           2462

TCTTCTTCAT ATGTATTTCT TTTTTTCCTC GCTTTCTCTG CCCACTTTTT           2512

TCTTCTGTCT TCTAGA                                                2528
```